United States Patent
Asama et al.

(10) Patent No.: US 10,398,741 B2
(45) Date of Patent: Sep. 3, 2019

(54) COMPOSITION

(71) Applicant: Yamada Bee Company, Inc., Tomata-gun, Okayama (JP)

(72) Inventors: Takashi Asama, Okayama (JP); Tomoyo Keishi, Okayama (JP); Shinobu Fukushima, Okayama (JP); Yuka Kimura, Okayama (JP); Tetuya Sado, Okayama (JP); Shinichiro Saito, Okayama (JP)

(73) Assignee: YAMADA BEE COMPANY, INC., Okayama (JP)

( * ) Notice: Subject to any disclaimer, the term of this patent is extended or adjusted under 35 U.S.C. 154(b) by 94 days.

(21) Appl. No.: 15/543,519

(22) PCT Filed: Jan. 12, 2016

(86) PCT No.: PCT/JP2016/050714
§ 371 (c)(1),
(2) Date: Jul. 13, 2017

(87) PCT Pub. No.: WO2016/117416
PCT Pub. Date: Jul. 28, 2016

(65) Prior Publication Data
US 2018/0000871 A1 Jan. 4, 2018

(30) Foreign Application Priority Data
Jan. 22, 2015 (JP) ................. 2015-010130

(51) Int. Cl.
*A61K 35/644* (2015.01)
*A23L 21/20* (2016.01)
*A23L 33/10* (2016.01)
*A23L 21/25* (2016.01)

(52) U.S. Cl.
CPC ............ *A61K 35/644* (2013.01); *A23L 21/20* (2016.08); *A23L 21/25* (2016.08); *A23L 33/10* (2016.08)

(58) Field of Classification Search
CPC .................................... A61K 36/00
See application file for complete search history.

(56) References Cited

U.S. PATENT DOCUMENTS 6,482,442 B1  11/2002  Dado
2015/0018791 A1  1/2015  Devenish et al.

FOREIGN PATENT DOCUMENTS

| CN | 1092317 A | 9/1994 |
|---|---|---|
| CN | 1336130 A | 2/2002 |
| CN | 101250508 A | 8/2008 |
| CN | 101305977 A | * 11/2008 |
| CN | 101305977 A | 11/2008 |
| CN | 104222728 A | 12/2014 |
| CN | 104273411 A | 1/2015 |
| ES | 2372196 A1 | 1/2012 |
| FR | 2463587 A1 | 2/1981 |
| JP | H07203874 A | 8/1995 |
| JP | H07264997 A | 10/1995 |
| JP | 2001061418 A | 3/2001 |
| JP | 2004/229575 A | 8/2004 |
| JP | 2007016014 A | 1/2007 |
| KR | 2003027482 A | * 4/2003 |
| KR | 2012/0030727 A | 3/2012 |
| KR | 2012/0030728 A | 3/2012 |
| RU | 2031599 C1 | 3/1995 |

OTHER PUBLICATIONS

International Search Report for PCT/JP2016/050714 dated Mar. 8, 2016, 2 pages.
International Preliminary Report on Patentability for PCT/JP2016/050714 dated Aug. 3, 2017, 7 pages.
Yamaguchi, Masayoshi, "Mitsubachi Kafunka Seibun no Atarashii Seiri Sayo to shite no Kotsuryo Zoshin Koka to sono Kotsusoshosho Yobo eno Tankai" (Bone mass increase effect as the new physiological function of bee pollen ingredient, and development of the effect to osteoporotic prevention), New Food Industry, vol. 51, No. 8, 2009, pp. 17-24, with partial English translation.
Communication issued by the European Patent Office dated Jun. 29, 2018 for European Patent Application No. 16740023.3, 9 pages.
Office Action issued by the Japan Patent Office dated Jan. 8, 2019 for Japanese Patent Application No. P2016-570583, 4 pages.

* cited by examiner

*Primary Examiner* — Qiuwen Mi
(74) *Attorney, Agent, or Firm* — Squire Patton Boggs (US) LLP

(57) ABSTRACT

The present invention provides a composition comprising: honey; bee pollen; royal jelly; and propolis, wherein the content of the honey is 70% by mass or more and less than 100% by mass relative to the whole amount of the composition; the content of the bee pollen is more than 0% by mass and 10% by mass or less in terms of solid content relative to the whole amount of the composition; the content of the royal jelly is more than 0% by mass and 10% by mass or less in terms of solid content relative to the whole amount of the composition; and the content of the propolis is more than 0% by mass and 10% by mass or less in terms of solid content relative to the whole amount of the composition.

6 Claims, No Drawings

COMPOSITION

TECHNICAL FIELD

The present invention relates to a composition.

BACKGROUND ART

Bee products such as honey, royal jelly, bee pollen, and propolis have been utilized as food and the like for many years and known to each have various physiological activities. For example, there are disclosed a bone mass-increasing composition (Patent Literature 1) containing water extract of bee pollen as an active component, an anti-fatigue composition containing a royal jelly purified product (Patent Literature 2), and the like.

CITATION LIST

Patent Literature

Patent Literature 1: JP 2007-16014 A
Patent Literature 2: JP 2001-61418 A

SUMMARY OF INVENTION

Technical Problem

The physiological activities of each of honey, royal jelly, bee pollen, and propolis when they are used singly have been known, but the physiological activities in the case of combining all of these bee products have not been known.

An object of the present invention is to provide a novel bee product composition having excellent physiological activities.

Solution to Problem

The present inventors have found that various excellent physiological activities are produced by combining honey, bee pollen, royal jelly, and propolis in specific ratios.

The present invention provides a composition comprising honey, bee pollen, royal jelly, and propolis (also referred to as "a bee product composition"), wherein the content of the honey is 70% by mass or more and less than 100% by mass relative to the whole amount of the composition; the content of the bee pollen is more than 0% by mass and 10% by mass or less in terms of solid content relative to the whole amount of the composition; the content of the royal jelly is more than 0% by mass and 10% by mass or less in terms of solid content relative to the whole amount of the composition; and the content of the propolis is more than 0% by mass and 10% by mass or less in terms of solid content relative to the whole amount of the composition. The composition has various excellent physiological activities.

In the composition, it is preferable that the honey be at least one selected from the group consisting of manuka honey, acacia honey, and honeydew honey, and it is more preferable that the honey be manuka honey and acacia honey. The above composition can generate higher physiological activity when the honey is these types of honey.

The above composition may be for alleviating asthenopia, for alleviating cold symptoms, for alleviating tinnitus, for alleviating dysuria, for alleviating palpitation and breathlessness, for improving the quality of sleep, for reducing mental stress, for alleviating vertigoes, for improving skin condition, for stimulating appetite, for alleviating nausea of the chest and the stomach, for improving constipation, for alleviating numbness of hands and feet, for lowering blood pressure, for reducing cholesterol, for alleviating tired feeling, for improving motivation, or for improving hair condition.

The invention relating to the bee product composition used for the above applications can also be said to be an invention relating to a composition for use in alleviating asthenopia, alleviating cold symptoms, alleviating tinnitus, alleviating dysuria, alleviating palpitation and breathlessness, improving the quality of sleep, reducing mental stress, alleviating vertigoes, improving skin condition, stimulating appetite, alleviating nausea of the chest and the stomach, improving constipation, alleviating numbness of hands and feet, lowering blood pressure, reducing cholesterol, alleviating tired feeling, improving motivation, or improving hair condition.

The invention relating to the bee product composition used for the above applications can also be said to be an invention relating to the use of the above bee product composition in the production of a composition for alleviating asthenopia, for alleviating cold symptoms, for alleviating tinnitus, for alleviating dysuria, for alleviating palpitation and breathlessness, for improving the quality of sleep, for reducing mental stress, for alleviating vertigoes, for improving skin condition, for stimulating appetite, for alleviating nausea of the chest and the stomach, for improving constipation, for alleviating numbness of hands and feet, for lowering blood pressure, for reducing cholesterol, for alleviating tired feeling, for improving motivation, or for improving hair condition.

The invention relating to the bee product composition used for the above applications can also be said to be an invention relating to a method for alleviating asthenopia, a method for alleviating cold symptoms, a method for alleviating tinnitus, a method for alleviating dysuria, a method for alleviating palpitation and breathlessness, a method for improving the quality of sleep, a method for reducing mental stress, a method for alleviating vertigoes, a method for improving skin condition, a method for stimulating appetite, a method for alleviating nausea of the chest and the stomach, a method for improving constipation, a method for alleviating numbness of hands and feet, a method for lowering blood pressure, a method for reducing cholesterol, a method for alleviating tired feeling, a method for improving motivation, or a method for improving hair condition, the method comprising a step of administering the above bee product composition to a subject in need thereof. It is preferable that the above subject be mammals, and it is more preferable that the subject be human.

The above composition may be food, health foods, functional foods, nutritional supplementary foods, supplements, or foods for specified health use for alleviating asthenopia, for alleviating cold symptoms, for alleviating tinnitus, for alleviating dysuria, for alleviating palpitation and breathlessness, for improving the quality of sleep, for reducing mental stress, for alleviating vertigoes, for improving skin condition, for stimulating appetite, for alleviating nausea of the chest and the stomach, for improving constipation, for alleviating numbness of hands and feet, for lowering blood pressure, for reducing cholesterol, for alleviating tired feeling, for improving motivation, or for improving hair condition.

Advantageous Effects of Invention

The present invention can provide a bee product composition having excellent physiological activity.

DESCRIPTION OF EMBODIMENTS

Hereinafter, embodiments for carrying out the present invention will be described in detail. However, the present invention is not limited to the following embodiments.

The bee product composition according to the present invention comprises honey, bee pollen, royal jelly, and propolis as active components.

(Honey)

The bee product composition according to the present invention comprises honey as one of the active components. Honey is a product that honeybees have produced using the syrup collected from vegetable nectar, sap, secretion of insects parasitic on plants, and the like, as the main raw material. The type of honey is not particularly limited, and examples that can be used include manuka honey, acacia honey, honeydew honey, clover honey, orange honey, milk vetch honey, rosemary honey, sunflower honey, rape-blossom honey, and coffee honey. Honey may be used individually or in combination of a plurality of types. It is preferable that, among them, honey be manuka honey, acacia honey, or honeydew honey, and it is more preferable that honey be a combination of manuka honey and acacia honey. When these types of honey are used, various physiological activities can be further increased.

The honey used for the bee product composition according to the present embodiment may be used directly as it is collected or may be used after purification treatment such as removal of protein, wax, foreign particles, debris of nests, and the like, and filtration, and treatment such as sterilization, drying, and/or concentration. The type of honeybees utilized for collecting honey is not particularly limited. Honey can be obtained, for example, as an apiculture product according to a conventional method.

The content of honey in the bee product composition is 70% by mass or more and less than 100% by mass; it is preferable that the content be 78% by mass or more and 97% by mass or less; it is more preferable that the content be 85% by mass or more and 95% by mass or less; it is further preferable that the content be 87% by mass or more and 93% by mass or less; and it is yet more preferable that the content be 89.5% by mass or more and 91.5% by mass or less, relative to the whole amount of the bee product composition. When the content of honey is in the above range, physiological activity can be further increased.

(Bee Pollen)

The bee product composition according to the present invention comprises bee pollen as one of the active components. The bee pollen is a mixture of pollen and nectar which honeybees have collected. The bee pollen may be used directly as it is collected or may be a treated bee pollen which has undergone treatment such as physical treatment such as grinding or crushing, drying treatment, extraction treatment, enzyme treatment, and fermentation treatment. The physical treatment can be performed, for example, by applying ultrasonic vibration to water containing bee pollen. Since it is said that pollen particles have a hard cell wall and low digestibility, it is preferable that bee pollen be a treated bee pollen. By breaking the cell wall of pollen by the above various treatments, it is possible to improve the digestion and absorption properties at the time when bee pollen is ingested.

The bee pollen used for the bee product composition according to the present embodiment is not particularly limited, but it is preferable that the bee pollen be derived from cistus. The type of honeybees utilized for collecting bee pollen is not particularly limited. Bee pollen can be obtained, for example, as an apiculture product according to a conventional method.

The content of bee pollen in the bee product composition according to the present embodiment is more than 0% by mass and 10% by mass or less; it is preferable that the content be 2% by mass or more and 8% by mass or less; it is more preferable that the content be 3% by mass or more and 7% by mass or less; it is further preferable that the content be 4% by mass or more and 6% by mass or less; and it is yet more preferable that the content be 4.5% by mass or more and 5.5% by mass or less, in terms of solid content relative to the whole amount of the bee product composition. When the content of bee pollen is in the above range, physiological activity can be further increased.

(Royal Jelly)

The bee product composition according to the present invention comprises royal jelly as one of the active components. The royal jelly is a milky material formed from a protein-rich transparent liquid material which a worker bee secretes from the hypopharyngeal gland and fatty acids which a worker bee secretes from the mandibular gland, or a material derived from the milky material. It is known that water, protein, carbohydrate, lipid, ash, free amino acids, vitamins, minerals, and the like are contained in the royal jelly. The royal jelly may be used directly as it is collected (raw royal jelly), or may be a treated royal jelly which is obtained by subjecting raw royal jelly to treatment. Raw royal jelly can be obtained, for example, as an apiculture product according to a conventional method. The type of honeybees utilized for collecting raw royal jelly is not particularly limited.

Examples of the treated royal jelly include a royal jelly concentrate or dilution obtained by concentrating or diluting raw royal jelly, royal jelly powder obtained by drying and pulverizing raw royal jelly, enzyme-hydrolyzed royal jelly obtained by treating raw royal jelly with a proteolytic enzyme, and organic solvent extract of royal jelly such as ethanol extract of royal jelly obtained by extracting raw royal jelly with an organic solvent such as ethanol. The treated royal jelly may be one obtained through a plurality of treatments. It is preferable that the royal jelly be enzyme-hydrolyzed royal jelly powder which has been enzyme-hydrolyzed and pulverized. The use of enzyme-hydrolyzed royal jelly powder is preferable because higher physiological activity and reduced allergenicity can be provided.

The royal jelly concentrate can be obtained, for example, by removing water from raw royal jelly. The royal jelly dilution can be obtained, for example, by adding water to raw royal jelly.

The royal jelly powder can be obtained, for example, by pulverizing the raw royal jelly by a known method in the art, such as freeze drying and spray drying. Further, the royal jelly powder may be obtained by grinding the raw royal jelly with a grinder (for example, a pinmill, a hammer mill, a ball mill, and a jet mill) after freeze drying or spray drying.

The enzyme-hydrolyzed royal jelly can be obtained, for example, by treating raw royal jelly with a proteolytic enzyme. Examples of the proteolytic enzyme include an enzyme having endopeptidase action, an enzyme having exopeptidase action, and an enzyme having both endopeptidase action and exopeptidase action. As the proteolytic enzyme, it may be an enzyme having at least one of endopeptidase action and exopeptidase action; an enzyme having at least endopeptidase action is preferred; and an enzyme having both endopeptidase action and exopeptidase action is more preferred. Here, the endopeptidase action is the action of decomposing peptide bonds of the non-terminal amino acids, and the exopeptidase action is the action of decomposing the peptide bonds of terminal amino acids.

Among the proteolytic enzymes, there are an enzyme having only exopeptidase action, an enzyme having only endopeptidase action, and an enzyme having both endopeptidase action and exopeptidase action. The enzyme having both endopeptidase action and exopeptidase action is regarded as "an enzyme having endopeptidase action" when the endopeptidase action is stronger, regarded as "an enzyme having exopeptidase action" when the exopeptidase activity is stronger, and regarded as "an enzyme having both endopeptidase action and exopeptidase action" when the endopeptidase action and the exopeptidase action are equal or substantially equal. Note that "equal or substantially equal" means that the ratio of endopeptidase action to exopeptidase action (activity ratio) is 0.8 to 1.2.

Specific examples of the enzyme having both endopeptidase action and exopeptidase action include pancreatin and pepsin. More specific examples of the enzyme having both endopeptidase action and exopeptidase action include *Streptomyces griseus*-produced peptidase (trade name: Actinase AS), *Aspergillus orizae*-produced peptidase (trade name: Protease A, Flavourzyme), and *Aspergillus melleus*-produced peptidase (trade name: Protease P).

Specific examples of the enzyme having exopeptidase action include carboxypeptidase, aminopeptidase, and exopeptidase derived from microorganisms such as lactic acid bacteria, *Aspergillus* bacteria, or *Rhizopus* bacteria. More specific examples of the enzyme having exopeptidase action include *Aspergillus orizae*-produced peptidase (trade name: Umamizyme G, Promod 192P, Promod 194P, Sumiteam FLAP), *Aspergillus sojae*-produced peptidase (trade name: Sternzyme B15024), *Aspergillus*-produced peptidase (trade name: Kokulase P), and *Rhizopus oryzae*-produced peptidase (trade name: Peptidase R).

Specific examples of the enzyme having endopeptidase action include endopeptidase derived from animals (for example, trypsin and chymotrypsin), endopeptidase derived from plants (for example, papain), and endopeptidase derived from microorganisms such as lactic acid bacteria, yeast, mold, *Bacillus subtilis*, or actinomycetes. More specific examples of the enzyme having endopeptidase action include *Bacillus subtilis*-produced peptidase (trade name: Orientase 22BF, Nucleicin), *Bacillus licheniformis*-produced peptidase (trade name: Alcalase), *Bacillus stearothermophilus*-produced peptidase (trade name: Protease S), *Bacillus amyloliquefaciens*-produced peptidase (trade name: Neutrase), and *Bacillus*-produced peptidase (trade name: Protamex).

The reaction conditions (the amount of a proteolytic enzyme used, the temperature during reaction, pH, reaction time, and the like) when raw royal jelly is treated with a proteolytic enzyme may be appropriately set depending on the type of the proteolytic enzyme to be used and the like. For example, when Actinase AS (Kaken Pharmaceutical Co., Ltd.) having both endopeptidase action and exopeptidase action is used as a proteolytic enzyme, illustrative reaction conditions include an amount of the proteolytic enzyme used of 1 g per 100 g of royal jelly, a temperature during reaction of 45 to 55° C., a pH of 8.5 to 9.5, and a reaction time of 2 to 4 hours.

The organic solvent extract of royal jelly can be obtained by extracting raw royal jelly, for example, by using an organic solvent such as ethanol, methanol, propanol, and acetone as a solvent. The extraction time can be appropriately set depending on the form of raw royal jelly used as a raw material, the type and the amount of solvent, the temperature and stirring conditions during extraction, and the like. After extraction, solids may be removed by filtration, centrifugal separation, or the like. Further, the extracted solution may be used directly as it is, or the extract may be used as a concentrate or powder after removing a solvent from the solution. It is preferable that the organic solvent extract of royal jelly be an ethanol extract of royal jelly.

Commercially available royal jelly may be used. Specific examples of royal jelly include Royal Jelly FD Power (manufactured by Nakahara Co., Ltd.), Royal Jelly Extract SF (manufactured by Matsuura Yakugyo Co., Ltd.), Deproteinized Royal Jelly Powder F (manufactured by Maruzen Pharmaceuticals Co., Ltd.), and Deproteinized Royal Jelly Extract (manufactured by API Inc.).

The content of royal jelly in the bee product composition according to the present embodiment is more than 0% by mass and 10% by mass or less; it is preferable that the content be 1% by mass or more and 7% by mass or less; it is more preferable that the content be 2% by mass or more and 5% by mass or less; it is further preferable that the content be 2.3% by mass or more and 4.5% by mass or less; and it is yet more preferable that the content be 2.8% by mass or more and 3.8% by mass or less, in terms of solid content relative to the whole amount of the bee product composition. When the content of royal jelly is in the above range, physiological activity can be further increased.

(Propolis)

The bee product composition according to the present invention comprises propolis as one of the active components. Propolis is a resinous or waxy material constituting the wall of a beehive of *Apis mellifera*. Propolis may be derived from any area of production, for example, Brazil, China, European countries, Oceania, United States, and the like; and propolis may be derived from any plant, for example, derived from *Baccharis dracunculifolia*, derived from *eucalyptus*, and the like. Further, propolis may be of any rank, such as super green and ultra green. The type of honeybees utilized for collecting propolis is not particularly limited. Propolis can be obtained, for example, as an apiculture product according to a conventional method.

Propolis may be a propolis original lump, or may be a treated propolis which is obtained by subjecting the propolis original lump to treatment such as grinding, supercritical extraction, water or hydrophilic organic solvent extraction, concentration or pulverization of an extract, or granulation of powder. Among them, a hydrophilic organic solvent extract obtained by hydrophilic organic solvent extraction of propolis is preferable since the active component of propolis is efficiently extracted with good balance in a short time. Ethanol is preferable as a hydrophilic organic solvent used for extraction.

The content of propolis in the bee product composition according to the present embodiment is more than 0% by mass and 10% by mass or less; it preferable that the content be 0.07% by mass or more and 7% by mass or less; it more preferable that the content be 0.2% by mass or more and 3.5% by mass or less; it is further preferable that the content be 0.3% by mass or more and 2% by mass or less; it is yet more preferable that the content be 0.5% by mass or more and 0.8% by mass or less; and it is particularly preferable that the content be 0.6% by mass or more and 0.75% by mass or less, in terms of solid content relative to the whole amount of the bee product composition. When the content of propolis is in the above range, physiological activity can be further increased.

The above bee product composition can be obtained by mixing each raw material.

(Alleviating Asthenopia)

The bee product composition of the present invention can alleviate asthenopia. Specifically, it is possible to significantly alleviate symptoms such as dimness of sight, oppressive feeling of eyes, spasm of eyelids, eye fatigue, and eye pain by ingesting the bee product composition according to the present embodiment. That is, it is possible to suppress the occurrence of symptoms, reduce the occurrence frequency of symptoms, or alleviate symptoms, such as dimness of sight, oppressive feeling of eyes, spasm of eyelids, eye fatigue, and eye pain, by ingesting the bee product composition according to the present embodiment. Therefore, the above bee product composition can be used for alleviating dimness of sight, for alleviating oppressive feeling of eyes, for alleviating spasm of eyelids, for alleviating eye fatigue, or for alleviating eye pain.

(Alleviating Cold Symptoms)

The bee product composition of the present invention can alleviate cold symptoms. Specifically, it is possible to significantly alleviate symptoms such as having a throat pain due to a cold, having a cough, having a coughing fit, having phlegm sticking, and having difficulty in breathing like choking by ingesting the bee product composition according to the present embodiment. That is, it is possible to suppress the occurrence of symptoms or reduce the occurrence frequency of symptoms, such as having a throat pain due to a cold, having a cough, having a coughing fit, having phlegm sticking, and having difficulty in breathing like choking, by ingesting the bee product composition according to the present embodiment. Therefore, the above bee product composition can be used for alleviating a throat pain due to a cold, for alleviating a cough, for alleviating phlegm, and for alleviating choking.

(Alleviating Tinnitus)

The bee product composition of the present invention can alleviate tinnitus. Examples of the symptoms of tinnitus include having an ear-plugged sensation like entering a tunnel and being bothered with a sound which does not bother other people, the sound being felt like an awful sound, and may also include having a bad feeling and nausea caused by tinnitus. It is possible to significantly alleviate symptoms such as having an ear-plugged sensation like entering a tunnel, being bothered with a sound which does not bother other people, the sound being felt like an awful sound, and tinnitus followed by a bad feeling and nausea by ingesting the bee product composition according to the present embodiment. That is, it is possible to suppress the occurrence of symptoms or reduce the occurrence frequency of symptoms, such as having an ear-plugged sensation like entering a tunnel, being bothered with a sound which does not bother other people, the sound being felt like an awful sound, and tinnitus followed by a bad feeling and nausea, by ingesting the bee product composition according to the present embodiment.

(Alleviating Dysuria)

The bee product composition of the present invention can alleviate dysuria. Examples of the symptoms of dysuria include urination time being long, not being able to urinate unless stress is applied to abdomen, and having a feeling of incomplete emptying of the bladder. It is possible to significantly alleviate symptoms such as urination time being long, not being able to urinate unless stress is applied to abdomen, and having a feeling of incomplete emptying of the bladder by ingesting the bee product composition according to the present embodiment. That is, it is possible to suppress the occurrence of symptoms or reduce the occurrence frequency of symptoms, such as urination time being long, not being able to urinate unless stress is applied to abdomen, and having a feeling of incomplete emptying of the bladder, by ingesting the bee product composition according to the present embodiment.

(Alleviating Palpitation and Breathlessness)

The bee product composition of the present invention can alleviate palpitation and breathlessness. Specifically, it is possible to significantly alleviate symptoms such as palpitation (feeling heart beating), breathlessness, arrhythmia (pulse intermission, irregular pulse), and having a feeling a sharp pain in the chest by ingesting the bee product composition according to the present embodiment. That is, it is possible to suppress the occurrence of symptoms or reduce the occurrence frequency of symptoms, such as palpitation, breathlessness, arrhythmia, and having a feeling a sharp pain in the chest, by ingesting the bee product composition according to the present embodiment. Therefore, the above bee product composition can be used for alleviating palpitation, for alleviating breathlessness, for alleviating arrhythmia, and for alleviating chest pain.

(Improving Quality of Sleep)

The bee product composition of the present invention can improve the quality of sleep or can improve insomnia. Examples of the insomnia include symptoms such as taking long time to fall asleep, waking at night, and being unable to sleep again after waking early morning. It is possible to improve symptoms such as having trouble falling asleep, waking at night, and being unable to sleep again after waking early morning by ingesting the bee product composition according to the present embodiment. That is, it is possible to suppress the occurrence of symptoms or reduce the occurrence frequency of symptoms, such as having trouble falling asleep, waking at night, and being unable to sleep again after waking early morning, by ingesting the bee product composition according to the present embodiment.

(Reducing Mental Stress)

The bee product composition of the present invention can reduce mental stress. Specifically, it is possible to significantly alleviate symptoms such as impatience (particularly, a feeling of impatience or a feeling of irritation) and awareness of mental stress by ingesting the bee product composition according to the present embodiment. That is, it is possible to suppress the occurrence of symptoms or reduce the occurrence frequency of symptoms, such as impatience and consciousness of mental stress, by ingesting the bee product composition according to the present embodiment. Therefore, the above bee product composition can be used for relieving impatience.

(Alleviating Vertigoes)

The bee product composition of the present invention can alleviate vertigoes. It is possible to significantly alleviate rotary vertigoes appearing as symptoms such as realizing as if you yourself and/or surroundings are turning by ingesting the bee product composition according to the present embodiment. That is, it is possible to suppress the occurrence of symptoms or reduce the occurrence frequency of symptoms, such as realizing as if you yourself and/or surroundings are turning, by ingesting the bee product composition according to the present embodiment. Therefore, the above bee product composition can be used for alleviating rotary vertigoes.

(Improving Skin Condition)

The bee product composition of the present invention can improve skin condition. Specifically, it is possible to significantly alleviate symptoms such as itchiness of the skin, drying of the skin, and a decrease in resilience or reboundability of the skin by ingesting the bee product composition according to the present embodiment. That is, it is possible to suppress the occurrence of symptoms or reduce the occurrence frequency of symptoms, such as itchiness of the skin, drying of the skin, and a decrease in resilience or reboundability of the skin, by ingesting the bee product composition according to the present embodiment.

(Stimulating Appetite)

The bee product composition of the present invention can stimulate appetite. Specifically, it is possible to significantly alleviate symptoms such as having a feeling of poorer appetite than usual by ingesting the bee product composition according to the present embodiment. That is, it is possible to suppress the occurrence of symptoms or reduce the occurrence frequency of symptoms, such as having a feeling of poorer appetite than usual, by ingesting the bee product composition according to the present embodiment. Therefore, the bee product composition according to the present embodiment can be used for alleviating loss of appetite.

(Alleviating Nausea of the Chest and the Stomach)

The bee product composition of the present invention can alleviate nausea of the chest and/or the stomach. Specifically, it is possible to significantly alleviate symptoms such as nausea of the chest and/or the stomach by ingesting the bee product composition according to the present embodiment. That is, it is possible to suppress the occurrence of symptoms or reduce the occurrence frequency of symptoms, such as nausea of the chest and/or the stomach, by ingesting the bee product composition according to the present embodiment.

(Improving Constipation)

The bee product composition of the present invention can improve constipation. Specifically, it is possible to significantly improve symptoms such as constipation by ingesting the bee product composition according to the present embodiment. That is, it is possible to suppress the occurrence of symptoms or reduce the occurrence frequency of symptoms, such as constipation, by ingesting the bee product composition according to the present embodiment.

(Alleviating Numbness of Hands and Feet)

The bee product composition of the present invention can alleviate numbness of hands and feet. Specifically, it is possible to significantly alleviate symptoms such as having a smarting feeling or a trembling feeling in hands and feet or other parts of the body by ingesting the bee product composition according to the present embodiment. That is, it is possible to suppress the occurrence of symptoms or reduce the occurrence frequency of symptoms, such as having a smarting feeling or a trembling feeling in hands and feet or other parts of the body, by ingesting the bee product composition according to the present embodiment.

(Lowering Blood Pressure)

The bee product composition of the present invention can lower blood pressure. Specifically, it is possible to significantly lower systolic and/or diastolic blood pressure by ingesting the bee product composition according to the present embodiment. Therefore, the bee product composition according to the present embodiment can be used for improving high blood pressure.

(Reducing Cholesterol)

The bee product composition of the present invention can reduce cholesterol. Specifically, it is possible to significantly reduce total cholesterol in serum by ingesting the bee product composition according to the present embodiment. Therefore, the bee product composition according to the present embodiment can be used for reducing total cholesterol in serum.

(Alleviating Tired Feeling)

The bee product composition of the present invention can alleviate tired feeling. Specifically, it is possible to significantly alleviate tired feeling by ingesting the bee product composition according to the present embodiment.

(Improving Motivation)

The bee product composition of the present invention can improve motivation. Specifically, it is possible to suppress symptoms or reduce the occurrence frequency of symptoms, such as realizing lack of motivation, by ingesting the bee product composition according to the present embodiment. Therefore, the bee product composition according to the present embodiment can also be used for alleviating a decrease in motivation.

(Improving Hair Condition)

The bee product composition of the present invention can improve hair condition. Specifically, it is possible to significantly alleviate symptoms such as a decrease in hair resilience and a decrease in hair thickness by ingesting the bee product composition according to the present embodiment. Therefore, the bee product composition according to the present embodiment can be used for improving hair resilience and for reducing a decrease in hair thickness.

The bee product composition of the present invention may comprise only honey, royal jelly, bee pollen, and propolis, which are active components, or may further comprise other components as long as they do not impart the effects of the present invention. Examples of other components include pharmaceutically acceptable components (for example, excipients, binding materials, lubricants, disintegrators, emulsifiers, surfactants, base agents, solubilizing agents, and suspending agents) and components acceptable as food (for example, minerals, vitamins, flavonoids, quinones, polyphenols, amino acids, nucleic acids, essential fatty acids, refrigerants, binders, sweeteners, disintegrators, lubricants, colorants, flavoring agents, stabilizers, preservatives, controlled-release agents, surfactants, solubilizers, and wetting agents).

The bee product composition of the present invention can be used for an adult with a weight of 60 kg in a dose of 1 mg or more and 10 g or less per day in terms of the amount of active components; it is preferable to use the composition in a dose of 50 mg or more and 8 g or less; and it is more preferable to use the composition in a dose of 1 g or more and 7 g or less. The dosage can be appropriately set in the above range depending on factors such as health condition of those who ingest the composition, the administration method, and a combination with other agents.

Generally, it is said that the preferred amount of ingestion standards per day of bee pollen for exhibiting desired bioactivity is about 1200 mg. Further, according to Japan Health Food & Nutrition Food Association, the amount of royal jelly ingestion standards per day is 500 to 3000 mg as royal jelly, and the amount of propolis ingestion standards per day is 100 to 500 mg as propolis. On the other hand, the bee product composition according to the present embodiment can exhibit a significant bioactive function by using honey, bee pollen, royal jelly, and propolis in combination, as compared with the case where these components are individually used. Therefore, even if the amounts of bee pollen, royal jelly, and propolis contained in the dosage per day of the bee product composition are each much less than the amount of the above ingestion standards, the composition can exhibit sufficiently high bioactivity.

The bee product composition of the present invention may be orally administered (ingested) or may be parenterally administered. As long as the amounts of the active components per day are in the ranges described above, the bee product composition of the present invention may be administered once a day or may be administered in a plurality of times, such as two times a day and three times a day.

The bee product compositions of the present invention may have any form including solids, liquids, and pastes, and may have any dosage form including tablets (including uncoated tablets, sugar-coated tablets, effervescent tablets, film-coated tablets, chewable tablets, and troches), capsules, pills, powders (powdered drugs), fine granules, granules, liquids and solutions, suspensions, emulsions, syrups, pastes, and injections (including those blended with distilled water or infusions such as amino acid infusions or electrolyte infusions to prepare a liquid at the time of use). These various preparations can be prepared, for example, by mixing honey, royal jelly, bee pollen, and propolis, which are active components, with other optional components and shaping the mixture into the above dosage forms.

The bee product composition of the present invention can be used as pharmaceuticals and food themselves, and can also be used by adding it to pharmaceuticals and food. It is preferable that food be a food of which a third-order function, that is, a physical condition adjustment function of food is emphasized. Examples of the physical condition adjustment function include a function of alleviating asthenopia, a function of alleviating cold symptoms, a function of alleviating tinnitus, a function of alleviating dysuria, a function of alleviating palpitation and breathlessness, a function of improving the quality of sleep, a function of reducing mental stress, a function of alleviating vertigoes, a function of improving skin condition, a function of stimulating appetite, a function of alleviating nausea of the chest and the stomach, a function of improving constipation, a function of alleviating numbness of hands and feet, a function of lowering blood pressure, a function of reducing cholesterol, a function of alleviating tired feeling, a function of improving motivation, and a function of improving hair condition. Examples of the food in which the third-order function of food is emphasized include health foods, functional foods, nutritional supplementary foods, supplements, and foods for specified health use.

The pharmaceuticals or food consisting of the bee product composition of the present invention or the pharmaceuticals or food comprising the bee product composition of the present invention may be for alleviating asthenopia, for alleviating cold symptoms, for alleviating tinnitus, for alleviating dysuria, for alleviating palpitation and breathlessness, for improving the quality of sleep, for reducing mental stress, for alleviating vertigoes, for improving skin condition, for stimulating appetite, for alleviating nausea of the chest and the stomach, for improving constipation, for alleviating numbness of hands and feet, for lowering blood pressure, for reducing cholesterol, for alleviating tired feeling, for improving motivation, or for improving hair condition. Further, labels may be attached to the above pharmaceuticals or food, the labels indicating the effect of alleviating asthenopia, the effect of alleviating cold symptoms, the effect of alleviating tinnitus, the effect of alleviating dysuria, the effect of alleviating palpitation and breathlessness, the effect of improving the quality of sleep, the effect of reducing mental stress, the effect of alleviating vertigoes, the effect of improving skin condition, the effect of stimulating appetite, the effect of alleviating nausea of the chest and the stomach, the effect of improving constipation, the effect of alleviating numbness of hands and feet or the effect of lowering blood pressure, the effect of reducing cholesterol, the effect of alleviating tired feeling, the effect of improving motivation, or the effect of improving hair condition.

The content of the bee product composition of the present invention in pharmaceuticals and food may be appropriately set depending on the type and the like of pharmaceuticals and food so that the amount of active components ingested per day will be in the ranges described above.

When the bee product composition of the present invention is used by adding it to food (for example, health foods, functional foods, nutritional supplementary foods, or foods for specified health use), the form of food is not particularly limited; and the food may be, for example, beverages (such as soft drinks such as coffee, juice, and tea beverages, milk beverages, lactic acid bacteria beverages, a yogurt drink, and a carbonated drink); spreads (such as custard cream); paste (such as fruit paste); western-style confectioneries (such as chocolate, a doughnut, a pie, a cream puff, gum, jelly, a candy, cookie, a cake, and a pudding); Japanese sweets (such as a rice cake stuffed with sweet beans, rice cake, steamed filled dumplings, sponge cake, boiled peas with honey and bean jam, and sweet bean paste); ices (such as ice cream, a popsicle, and sherbet); food (such as curry, a beef bowl, risotto, miso soup, soup, meat sauce, a pasta, pickles, and jam); and seasonings (such as dressing, sprinkle condiment for rice, a chemical seasoning, and a soup packet).

A method for producing pharmaceuticals or food to which the bee product composition of the present invention is added is not particularly limited, but can appropriately follow a known method. For example, it is possible to obtain pharmaceuticals or food used for the above applications by mixing the bee product composition of the present invention with an intermediate product or an end product in the production process of the pharmaceuticals or food.

EXAMPLES

Hereinafter, the present invention will be more specifically described based on Examples. However, the present invention is not limited to the following Examples.

[Test Method]
A bee product composition was produced by mixing the raw materials shown in Table 1.

TABLE 1

| Raw material name | | Blending ratio (% by mass) |
|---|---|---|
| Honey | Manuka honey | 45.454 |
| | Acacia honey | 45.454 |
| | Bee pollen | 5.050 |
| | Royal jelly | 3.367 |
| | Propolis extract | 0.674 |
| | Vitamin C (L-ascorbic acid) | 0.001 |
| | Total | 100.0 |

In the above Table 1, the details of each raw material are as follows.
Manuka honey: manuka honey from New Zealand
Acacia honey: acacia honey from Romania
Bee pollen: bee pollen (cistus) coarse powder from Spain
Royal jelly: royal jelly enzyme-treated powder RJ-MF from China (royal jelly which is treated with proteolytic enzyme, and then dried and pulverized)

Propolis: concentrated propolis extract from Brazil (an ethanolic extract, solid content: 70% by mass)

Test Example 1

Two hundred and fifty healthy volunteers were selected as subjects, and they drank the bee product composition described above (3 g/day) every day for 8 weeks. At the time of entry (before start drinking) and after drinking for 8 weeks, a questionnaire was used to evaluate various symptoms by four-step scores (1: hardly ever occurs, 2: rarely occurs, 3: sometimes occurs, 4: frequently occurs). A cross-tabulation table was prepared from the results of the questionnaire, and the scores before start drinking and after drinking were analyzed by the Wilcoxon signed rank sum test. Further, 41 subjects who had been usually measuring blood pressure with an automated sphygmomanometer among the above 250 persons were asked about the systolic/diastolic blood pressure at the time of rising, at the time of entry (before start drinking) and after drinking for 8 weeks.

[Results]

For each symptom, the question items and the test results of questionnaire evaluation are shown in Tables 2 to 31. The results of sphygmomanometry are shown in Table 32. The underline in the tables shows that the improvement was observed after drinking for 8 weeks.

(Asthenopia)

TABLE 2

Dimness of sight

| At the time of entry (before start drinking) | After drinking for 8 weeks | | | | | |
|---|---|---|---|---|---|---|
| | (1) Hardly ever occurs | (2) Rarely occurs | (3) Sometimes occurs | (4) Frequently occurs | Total | Within-subgroup test |
| (1) Hardly ever occurs | 222 | 0 | 0 | 0 | 222 | p = 0.0001 |
| (2) Rarely occurs | 5 | 10 | 0 | 0 | 15 | |
| (3) Sometimes occurs | 2 | 4 | 5 | 0 | 11 | |
| (4) Frequently occurs | 0 | 0 | 3 | 0 | 3 | |
| Total | 229 | 14 | 8 | 0 | 251 | |

TABLE 3

Oppressive feeling of eyes

| At the time of entry (before start drinking) | After drinking for 8 weeks | | | | | |
|---|---|---|---|---|---|---|
| | (1) Hardly ever occurs | (2) Rarely occurs | (3) Sometimes occurs | (4) Frequently occurs | Total | Within-subgroup test |
| (1) Hardly ever occurs | 216 | 0 | 1 | 0 | 217 | p = 0.0200 |
| (2) Rarely occurs | 3 | 20 | 0 | 0 | 23 | |
| (3) Sometimes occurs | 2 | 3 | 3 | 0 | 8 | |
| (4) Frequently occurs | 0 | 1 | 2 | 0 | 3 | |
| Total | 221 | 24 | 6 | 0 | 251 | |

TABLE 4

Spasm of eyelids

| At the time of entry (before start drinking) | After drinking for 8 weeks | | | | | |
|---|---|---|---|---|---|---|
| | (1) Hardly ever occurs | (2) Rarely occurs | (3) Sometimes occurs | (4) Frequently occurs | Total | Within-subgroup test |
| (1) Hardly ever occurs | 171 | 8 | 1 | 0 | 180 | p < 0.0001 |
| (2) Rarely occurs | 31 | 23 | 0 | 0 | 54 | |

TABLE 4-continued

| | Spasm of eyelids | | | | | |
|---|---|---|---|---|---|---|
| | After drinking for 8 weeks | | | | | |
| At the time of entry (before start drinking) | (1) Hardly ever occurs | (2) Rarely occurs | (3) Sometimes occurs | (4) Frequently occurs | Total | Within-subgroup test |
| (3) Sometimes occurs | 1 | 7 | 2 | 0 | 10 | |
| (4) Frequently occurs | 0 | 0 | 2 | 1 | 3 | |
| Total | 203 | 38 | 5 | 1 | 247 | |

TABLE 5

| | Eye fatigue | | | | | |
|---|---|---|---|---|---|---|
| | After drinking for 8 weeks | | | | | |
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 194 | 0 | 0 | 0 | 194 | $p = 0.0048$ |
| (2) Rarely occurs | 3 | 25 | 1 | 1 | 30 | |
| (3) Sometimes occurs | 6 | 2 | 13 | 0 | 21 | |
| (4) Frequently occurs | 1 | 0 | 2 | 3 | 6 | |
| Total | 204 | 27 | 16 | 4 | 251 | |

TABLE 6

| | Eye pain | | | | | |
|---|---|---|---|---|---|---|
| | After drinking for 8 weeks | | | | | |
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 219 | 0 | 0 | 0 | 219 | $p = 0.0021$ |
| (2) Rarely occurs | 9 | 13 | 2 | 0 | 24 | |
| (3) Sometimes occurs | 1 | 4 | 1 | 0 | 6 | |
| (4) Frequently occurs | 0 | 0 | 1 | 1 | 2 | |
| Total | 229 | 17 | 4 | 1 | 251 | |

(Cold)

TABLE 7

Having a throat pain due to a cold

|  | After drinking for 8 weeks | | | | | |
|---|---|---|---|---|---|---|
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 219 | 1 | 0 | 0 | 220 | $p < 0.0001$ |
| (2) Rarely occurs | 11 | 8 | 0 | 0 | 19 | |
| (3) Sometimes occurs | 2 | 4 | 1 | 0 | 7 | |
| (4) Frequently occurs | 1 | 1 | 3 | 0 | 5 | |
| Total | 233 | 14 | 4 | 0 | 251 | |

TABLE 8

Having a cough or having a coughing fit

|  | After drinking for 8 weeks | | | | | |
|---|---|---|---|---|---|---|
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 226 | 0 | 0 | 0 | 226 | $p = 0.0078$ |
| (2) Rarely occurs | 4 | 11 | 0 | 0 | 15 | |
| (3) Sometimes occurs | 0 | 3 | 3 | 0 | 6 | |
| (4) Frequently occurs | 0 | 0 | 1 | 1 | 2 | |
| Total | 230 | 14 | 4 | 1 | 249 | |

TABLE 9

Having phlegm sticking

|  | After drinking for 8 weeks | | | | | |
|---|---|---|---|---|---|---|
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 220 | 1 | 0 | 0 | 221 | $p = 0.0391$ |
| (2) Rarely occurs | 5 | 18 | 0 | 0 | 23 | |
| (3) Sometimes occurs | 0 | 3 | 3 | 0 | 6 | |
| (4) Frequently occurs | 0 | 0 | 0 | 1 | 1 | |
| Total | 225 | 22 | 3 | 1 | 251 | |

TABLE 10

Having difficulty in breathing like choking

| At the time of entry (before start drinking) | After drinking for 8 weeks | | | | | Within-subgroup test |
|---|---|---|---|---|---|---|
| | (1) Hardly ever occurs | (2) Rarely occurs | (3) Sometimes occurs | (4) Frequently occurs | Total | |
| (1) Hardly ever occurs | 224 | 1 | 0 | 0 | 225 | p = 0.0027 |
| (2) Rarely occurs | 5 | 10 | 0 | 0 | 15 | |
| (3) Sometimes occurs | 2 | 3 | 3 | 0 | 8 | |
| (4) Frequently occurs | 1 | 0 | 1 | 1 | 3 | |
| Total | 232 | 14 | 4 | 1 | 251 | |

(Tinnitus)

TABLE 11

Ear-plugged sensation like entering a tunnel

| At the time of entry (before start drinking) | After drinking for 8 weeks | | | | | Within-subgroup test |
|---|---|---|---|---|---|---|
| | (1) Hardly ever occurs | (2) Rarely occurs | (3) Sometimes occurs | (4) Frequently occurs | Total | |
| (1) Hardly ever occurs | 223 | 0 | 0 | 0 | 223 | p = 0.0313 |
| (2) Rarely occurs | 2 | 18 | 0 | 0 | 20 | |
| (3) Sometimes occurs | 1 | 2 | 1 | 0 | 4 | |
| (4) Frequently occurs | 0 | 0 | 1 | 1 | 2 | |
| Total | 226 | 20 | 2 | 1 | 249 | |

TABLE 12

Being bothered with a sound which does not bother other people, the sound being felt like an awful sound

| At the time of entry (before start drinking) | After drinking for 8 weeks | | | | | Within-subgroup test |
|---|---|---|---|---|---|---|
| | (1) Hardly ever occurs | (2) Rarely occurs | (3) Sometimes occurs | (4) Frequently occurs | Total | |
| (1) Hardly ever occurs | 225 | 0 | 0 | 0 | 225 | p = 0.0156 |
| (2) Rarely occurs | 5 | 16 | 0 | 0 | 21 | |
| (3) Sometimes occurs | 1 | 1 | 2 | 0 | 4 | |
| (4) Frequently occurs | 0 | 0 | 0 | 0 | 0 | |
| Total | 231 | 17 | 2 | 0 | 250 | |

TABLE 13

Having a bad feeling and nausea

| | After drinking for 8 weeks | | | | | |
|---|---|---|---|---|---|---|
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 233 | 0 | 0 | 0 | 233 | p = 0.0313 |
| (2) Rarely occurs | 2 | 9 | 0 | 0 | 11 | |
| (3) Sometimes occurs | 0 | 2 | 1 | 0 | 3 | |
| (4) Frequently occurs | 0 | 0 | 2 | 1 | 3 | |
| Total | 235 | 11 | 3 | 1 | 250 | |

(Dysuria)

TABLE 14

Urination time is long

| | After drinking for 8 weeks | | | | | |
|---|---|---|---|---|---|---|
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 222 | 1 | 0 | 0 | 223 | p = 0.0391 |
| (2) Rarely occurs | 5 | 14 | 0 | 0 | 19 | |
| (3) Sometimes occurs | 0 | 2 | 6 | 0 | 8 | |
| (4) Frequently occurs | 0 | 0 | 1 | 0 | 1 | |
| Total | 227 | 17 | 7 | 0 | 251 | |

TABLE 15

Being unable to urinate unless stress is applied to abdomen

| | After drinking for 8 weeks | | | | | |
|---|---|---|---|---|---|---|
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 213 | 2 | 0 | 0 | 215 | p = 0.0048 |
| (2) Rarely occurs | 5 | 16 | 0 | 0 | 21 | |
| (3) Sometimes occurs | 2 | 5 | 4 | 0 | 11 | |
| (4) Frequently occurs | 1 | 0 | 0 | 0 | 1 | |
| Total | 221 | 23 | 4 | 0 | 248 | |

TABLE 16

A feeling of incomplete emptying of the bladder

| At the time of entry (before start drinking) | After drinking for 8 weeks | | | | | Within-subgroup test |
|---|---|---|---|---|---|---|
| | (1) Hardly ever occurs | (2) Rarely occurs | (3) Sometimes occurs | (4) Frequently occurs | Total | |
| (1) Hardly ever occurs | 221 | 1 | 0 | 0 | 222 | p = 0.0063 |
| (2) Rarely occurs | 8 | 10 | 0 | 0 | 18 | |
| (3) Sometimes occurs | 0 | 2 | 3 | 0 | 5 | |
| (4) Frequently occurs | 0 | 0 | 1 | 2 | 3 | |
| Total | 229 | 13 | 4 | 2 | 248 | |

TABLE 17

Feeling heart beating

| At the time of entry (before start drinking) | After drinking for 8 weeks | | | | | Within-subgroup test |
|---|---|---|---|---|---|---|
| | (1) Hardly ever occurs | (2) Rarely occurs | (3) Sometimes occurs | (4) Frequently occurs | Total | |
| (1) Hardly ever occurs | 230 | 0 | 0 | 0 | 230 | p = 0.0313 |
| (2) Rarely occurs | 4 | 10 | 0 | 0 | 14 | |
| (3) Sometimes occurs | 0 | 2 | 2 | 0 | 4 | |
| (4) Frequently occurs | 0 | 0 | 0 | 0 | 0 | |
| Total | 234 | 12 | 2 | 0 | 248 | |

TABLE 18

Breathlessness

| At the time of entry (before start drinking) | After drinking for 8 weeks | | | | | Within-subgroup test |
|---|---|---|---|---|---|---|
| | (1) Hardly ever occurs | (2) Rarely occurs | (3) Sometimes occurs | (4) Frequently occurs | Total | |
| (1) Hardly ever occurs | 225 | 0 | 0 | 0 | 225 | p = 0.0078 |
| (2) Rarely occurs | 4 | 13 | 0 | 0 | 17 | |
| (3) Sometimes occurs | 0 | 3 | 4 | 0 | 7 | |
| (4) Frequently occurs | 0 | 0 | 1 | 0 | 1 | |
| Total | 229 | 16 | 5 | 0 | 250 | |

TABLE 19

Pulse intermission or irregular pulse

After drinking for 8 weeks

| At the time of entry (before start drinking) | (1) Hardly ever occurs | (2) Rarely occurs | (3) Sometimes occurs | (4) Frequently occurs | Total | Within-subgroup test |
|---|---|---|---|---|---|---|
| (1) Hardly ever occurs | 232 | 0 | 0 | 0 | 232 | p = 0.0313 |
| (2) Rarely occurs | 4 | 7 | 0 | 0 | 11 | |
| (3) Sometimes occurs | 0 | 1 | 1 | 0 | 2 | |
| (4) Frequently occurs | 0 | 0 | 1 | 0 | 1 | |
| Total | 236 | 8 | 2 | 0 | 246 | |

TABLE 20

Feeling a sharp pain in the chest

After drinking for 8 weeks

| At the time of entry (before start drinking) | (1) Hardly ever occurs | (2) Rarely occurs | (3) Sometimes occurs | (4) Frequently occurs | Total | Within-subgroup test |
|---|---|---|---|---|---|---|
| (1) Hardly ever occurs | 227 | 0 | 0 | 0 | 227 | p = 0.0156 |
| (2) Rarely occurs | 4 | 7 | 0 | 0 | 11 | |
| (3) Sometimes occurs | 0 | 2 | 1 | 0 | 3 | |
| (4) Frequently occurs | 0 | 0 | 1 | 0 | 1 | |
| Total | 231 | 9 | 2 | 0 | 242 | |

(Quality of Sleep)

TABLE 21

Taking long time to fall asleep

After drinking for 8 weeks

| At the time of entry (before start drinking) | (1) Hardly ever occurs | (2) Rarely occurs | (3) Sometimes occurs | (4) Frequently occurs | Total | Within-subgroup test |
|---|---|---|---|---|---|---|
| (1) Hardly ever occurs | 203 | 3 | 0 | 0 | 206 | p < 0.0001 |
| (2) Rarely occurs | 13 | 21 | 0 | 0 | 34 | |
| (3) Sometimes occurs | 3 | 3 | 5 | 0 | 11 | |
| (4) Frequently occurs | 0 | 0 | 0 | 0 | 0 | |
| Total | 219 | 27 | 5 | 0 | 251 | |

TABLE 22

Waking at night

| At the time of entry (before start drinking) | After drinking for 8 weeks | | | | | |
|---|---|---|---|---|---|---|
| | (1) Hardly ever occurs | (2) Rarely occurs | (3) Sometimes occurs | (4) Frequently occurs | Total | Within-subgroup test |
| (1) Hardly ever occurs | 228 | 0 | 0 | 0 | 228 | p = 0.0020 |
| (2) Rarely occurs | 6 | 12 | 0 | 0 | 18 | |
| (3) Sometimes occurs | 1 | 2 | 1 | 0 | 4 | |
| (4) Frequently occurs | 0 | 0 | 1 | 0 | 1 | |
| Total | 235 | 14 | 2 | 0 | 251 | |

TABLE 23

Being unable to sleep again after waking early morning

| At the time of entry (before start drinking) | After drinking for 8 weeks | | | | | |
|---|---|---|---|---|---|---|
| | (1) Hardly ever occurs | (2) Rarely occurs | (3) Sometimes occurs | (4) Frequently occurs | Total | Within-subgroup test |
| (1) Hardly ever occurs | 213 | 3 | 0 | 0 | 216 | p = 0.0768 |
| (2) Rarely occurs | 8 | 18 | 1 | 0 | 27 | |
| (3) Sometimes occurs | 0 | 4 | 4 | 0 | 8 | |
| (4) Frequently occurs | 0 | 0 | 0 | 0 | 0 | |
| Total | 221 | 25 | 5 | 0 | 251 | |

(Mental Stress)

TABLE 24

Feeling impatient or irritated

| At the time of entry (before start drinking) | After drinking for 8 weeks | | | | | |
|---|---|---|---|---|---|---|
| | (1) Hardly ever occurs | (2) Rarely occurs | (3) Sometimes occurs | (4) Frequently occurs | Total | Within-subgroup test |
| (1) Hardly ever occurs | 222 | 0 | 0 | 0 | 222 | p = 0.0654 |
| (2) Rarely occurs | 3 | 13 | 0 | 0 | 16 | |
| (3) Sometimes occurs | 0 | 5 | 5 | 2 | 12 | |
| (4) Frequently occurs | 0 | 0 | 1 | 0 | 1 | |
| Total | 225 | 18 | 6 | 2 | 251 | |

TABLE 25

| | Feeling mental stress | | | | | |
|---|---|---|---|---|---|---|
| | After drinking for 8 weeks | | | | | |
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 216 | 1 | 0 | 0 | 217 | p = 0.0129 |
| (2) Rarely occurs | 6 | 19 | 1 | 0 | 26 | |
| (3) Sometimes occurs | 0 | 5 | 2 | 0 | 7 | |
| (4) Frequently occurs | 0 | 0 | 1 | 0 | 1 | |
| Total | 222 | 25 | 4 | 0 | 251 | |

(Vertigoes)

TABLE 26

| | Realizing as if you and/or your surroundings are turning | | | | | |
|---|---|---|---|---|---|---|
| | After drinking for 8 weeks | | | | | |
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 227 | 0 | 0 | 0 | 227 | p = 0.0156 |
| (2) Rarely occurs | 4 | 7 | 0 | 0 | 11 | |
| (3) Sometimes occurs | 0 | 2 | 1 | 0 | 3 | |
| (4) Frequently occurs | 0 | 0 | 1 | 0 | 1 | |
| Total | 231 | 9 | 2 | 0 | 242 | |

(Skin Condition)

TABLE 27

| | Itchiness of the skin | | | | | |
|---|---|---|---|---|---|---|
| | After drinking for 8 weeks | | | | | |
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 222 | 2 | 0 | 0 | 224 | p = 0.0225 |
| (2) Rarely occurs | 8 | 12 | 0 | 0 | 20 | |
| (3) Sometimes occurs | 0 | 2 | 3 | 0 | 5 | |
| (4) Frequently occurs | 0 | 0 | 1 | 0 | 1 | |
| Total | 230 | 16 | 4 | 0 | 250 | |

(Stimulating Appetite)

TABLE 28

Having poorer appetite than usual

| | After drinking for 8 weeks | | | | | |
|---|---|---|---|---|---|---|
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 224 | 0 | 0 | 0 | 224 | $p = 0.0005$ |
| (2) Rarely occurs | 7 | 9 | 0 | 0 | 16 | |
| (3) Sometimes occurs | 2 | 2 | 3 | 0 | 7 | |
| (4) Frequently occurs | 1 | 0 | 0 | 0 | 1 | |
| Total | 234 | 11 | 3 | 0 | 248 | |

(Nausea of the Chest and the Stomach)

TABLE 29

Nausea of the chest and the stomach

| | After drinking for 8 weeks | | | | | |
|---|---|---|---|---|---|---|
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 231 | 0 | 0 | 0 | 231 | $p = 0.0039$ |
| (2) Rarely occurs | 4 | 9 | 0 | 0 | 13 | |
| (3) Sometimes occurs | 0 | 4 | 1 | 0 | 5 | |
| (4) Frequently occurs | 0 | 0 | 1 | 0 | 1 | |
| Total | 235 | 13 | 2 | 0 | 250 | |

(Constipation)

TABLE 30

Constipation

| | After drinking for 8 weeks | | | | | |
|---|---|---|---|---|---|---|
| At the time of entry (before start drinking) | (1) Hardly ever occurs | (2) Rarely occurs | (3) Sometimes occurs | (4) Frequently occurs | Total | Within-subgroup test |
| (1) Hardly ever occurs | 217 | 0 | 0 | 0 | 217 | $p < 0.0001$ |
| (2) Rarely occurs | 12 | 12 | 1 | 0 | 25 | |
| (3) Sometimes occurs | 2 | 2 | 1 | 0 | 5 | |
| (4) Frequently occurs | 0 | 0 | 2 | 0 | 2 | |
| Total | 231 | 14 | 4 | 0 | 249 | |

(Numbness of Hands and Feet)

TABLE 31

Having a smarting feeling or a trembling feeling in the hands and feet or the body

| At the time of entry (before start drinking) | After drinking for 8 weeks | | | | | Within-subgroup test |
|---|---|---|---|---|---|---|
| | (1) Hardly ever occurs | (2) Rarely occurs | (3) Sometimes occurs | (4) Frequently occurs | Total | |
| (1) Hardly ever occurs | 203 | 4 | 0 | 0 | 207 | p < 0.0001 |
| (2) Rarely occurs | 26 | 8 | 0 | 0 | 34 | |
| (3) Sometimes occurs | 2 | 2 | 2 | 0 | 6 | |
| (4) Frequently occurs | 0 | 0 | 2 | 0 | 2 | |
| Total | 231 | 14 | 4 | 0 | 249 | |

(Lowering Blood Pressure)

TABLE 32

| | At the time of entry (before start drinking) | After drinking for 8 weeks | Within-subgroup test |
|---|---|---|---|
| Systolic blood pressure (mmHg) | 133.4 ± 12.96 | 131.2 ± 11.94 | p = 0.053 |
| Diastolic blood pressure (mmHg) | 85.3 ± 10.42 | 84.8 ± 9.73 | p = 0.254 |

Test Example 2

Eleven healthy volunteers were selected as subjects, and they drank the bee product composition described above (6 g/day) every day for 4 weeks. At the time of entry (before start drinking) and after drinking for 4 weeks, the total cholesterol value in blood was measured, and a questionnaire was used to evaluate various subjective symptoms by the following six-step scores. The scores before and after drinking were analyzed by the Wilcoxon signed rank sum test.

[Results]

The measurement results of the total cholesterol are shown in Table 33. The scores and the test results of questionnaire evaluation for each symptom are shown in Tables 34 to 41. The underline in the tables shows that the improvement was observed after drinking for 4 weeks.

(Total Cholesterol)

TABLE 33

| | At the time of entry (before start drinking) | After drinking for 4 weeks | Within-subgroup test |
|---|---|---|---|
| Total cholesterol (mg/dl) | 208 ± 33 | 197 ± 26 | p = 0.018 |

(Tired Feeling)

TABLE 34

Being afflicted with a tired feeling

| At the time of entry (before start drinking) | After drinking for 4 weeks | | | | | | Total | Within-subgroup test |
|---|---|---|---|---|---|---|---|---|
| | 0 | 1 | 2 | 3 | 4 | 5 | | |
| 0 | 2 | 0 | 0 | 0 | 0 | 0 | 2 | p = 0.008 |
| 1 | 0 | 0 | 0 | 0 | 0 | 0 | 0 | |
| 2 | 0 | 3 | 1 | 0 | 0 | 0 | 4 | |
| 3 | 2 | 0 | 1 | 0 | 0 | 0 | 3 | |
| 4 | 1 | 0 | 1 | 0 | 0 | 0 | 2 | |
| 5 | 0 | 0 | 0 | 0 | 0 | 0 | 0 | |
| Total | 5 | 3 | 3 | 0 | 0 | 0 | 11 | |

No: 0, Yes: slight [1-2-3-4-5] serious (Asthenopia)

TABLE 35

Being afflicted with asthenopia

| At the time of entry (before start drinking) | After drinking for 4 weeks | | | | | | Total | Within-subgroup test |
|---|---|---|---|---|---|---|---|---|
| | 0 | 1 | 2 | 3 | 4 | 5 | | |
| 0 | 3 | 0 | 0 | 0 | 0 | 0 | 3 | p = 0.031 |
| 1 | 1 | 0 | 0 | 0 | 0 | 0 | 1 | |
| 2 | 3 | 0 | 0 | 0 | 0 | 0 | 3 | |
| 3 | 1 | 0 | 0 | 1 | 0 | 0 | 2 | |
| 4 | 0 | 0 | 0 | 1 | 0 | 0 | 1 | |
| 5 | 0 | 0 | 0 | 0 | 0 | 1 | 1 | |
| Total | 8 | 0 | 0 | 2 | 0 | 1 | 11 | |

No: 0, Yes: slight [1-2-3-4-5] serious (Motivation)

TABLE 36

Feeling lack of motivation

| At the time of entry (before start drinking) | After drinking for 4 weeks | | | | | | Total | Within-subgroup test |
|---|---|---|---|---|---|---|---|---|
| | 0 | 1 | 2 | 3 | 4 | 5 | | |
| 0 | 1 | 0 | 0 | 0 | 0 | 0 | 1 | p = 0.016 |
| 1 | 3 | 1 | 0 | 0 | 0 | 0 | 4 | |

TABLE 36-continued

Feeling lack of motivation

| At the time of entry (before start drinking) | After drinking for 4 weeks | | | | | | Within-subgroup test |
|---|---|---|---|---|---|---|---|
| | 0 | 1 | 2 | 3 | 4 | 5 | Total |
| 2 | 2 | 0 | 2 | 0 | 0 | 0 | 4 |
| 3 | 0 | 1 | 0 | 0 | 0 | 0 | 1 |
| 4 | 0 | 0 | 0 | 0 | 0 | 0 | 0 |
| 5 | 0 | 1 | 0 | 0 | 0 | 0 | 1 |
| Total | 6 | 3 | 2 | 0 | 0 | 0 | 11 |

No: 0, Yes: very occasionally [1-2-3-4-5] frequently (Skin Condition)

TABLE 37

Skin condition

| At the time of entry (before start drinking) | After drinking for 4 weeks | | | | | | Total | Within-subgroup test |
|---|---|---|---|---|---|---|---|---|
| | 0 | 1 | 2 | 3 | 4 | 5 | | |
| 0 | 1 | 1 | 0 | 0 | 0 | 0 | 2 | p = 0.043 |
| 1 | 1 | 0 | 0 | 0 | 0 | 0 | 1 | |
| 2 | 3 | 1 | 0 | 1 | 0 | 0 | 5 | |
| 3 | 1 | 1 | 0 | 1 | 0 | 0 | 3 | |
| 4 | 0 | 0 | 0 | 0 | 0 | 0 | 0 | |
| 5 | 0 | 0 | 0 | 0 | 0 | 0 | 0 | |
| Total | 6 | 3 | 0 | 2 | 0 | 0 | 11 | |

Good: 0, Poor: slightly poor [1-2-3-4-5] very poor

TABLE 38

Being bothered with skin dryness

| At the time of entry (before start drinking) | After drinking for 4 weeks | | | | | | Total | Within-subgroup test |
|---|---|---|---|---|---|---|---|---|
| | 0 | 1 | 2 | 3 | 4 | 5 | | |
| 0 | 0 | 0 | 0 | 0 | 0 | 0 | 0 | p = 0.001 |
| 1 | 2 | 0 | 0 | 0 | 0 | 0 | 2 | |
| 2 | 1 | 2 | 0 | 0 | 0 | 0 | 3 | |
| 3 | 1 | 0 | 2 | 0 | 0 | 0 | 3 | |
| 4 | 0 | 1 | 0 | 1 | 0 | 0 | 2 | |
| 5 | 1 | 0 | 0 | 0 | 0 | 0 | 1 | |
| Total | 5 | 3 | 2 | 1 | 0 | 0 | 11 | |

Not be bothered: 0, Bothered: slightly poor [1-2-3-4-5] very poor

TABLE 39

Skin resilience and reboundability

| At the time of entry (before start drinking) | After drinking for 4 weeks | | | | | | Total | Within-subgroup test |
|---|---|---|---|---|---|---|---|---|
| | 0 | 1 | 2 | 3 | 4 | 5 | | |
| 0 | 3 | 0 | 0 | 0 | 0 | 0 | 3 | p = 0.016 |
| 1 | 0 | 0 | 0 | 0 | 0 | 0 | 0 | |
| 2 | 2 | 0 | 0 | 0 | 0 | 0 | 2 | |
| 3 | 1 | 1 | 0 | 0 | 0 | 0 | 2 | |
| 4 | 1 | 0 | 0 | 2 | 1 | 0 | 4 | |
| 5 | 0 | 0 | 0 | 0 | 0 | 0 | 0 | |
| Total | 7 | 1 | 0 | 2 | 1 | 0 | 11 | |

Yes: 0, No: not so much [1-2-3-4-5] entirely not (Hair Condition)

TABLE 40

Being bothered with hair resilience

| At the time of entry (before start drinking) | After drinking for 4 weeks | | | | | | Total | Within-subgroup test |
|---|---|---|---|---|---|---|---|---|
| | 0 | 1 | 2 | 3 | 4 | 5 | | |
| 0 | 1 | 0 | 0 | 0 | 0 | 0 | 1 | p = 0.008 |
| 1 | 2 | 2 | 0 | 0 | 0 | 0 | 4 | |
| 2 | 0 | 2 | 0 | 0 | 0 | 0 | 2 | |
| 3 | 0 | 0 | 0 | 0 | 0 | 0 | 0 | |
| 4 | 1 | 0 | 1 | 0 | 0 | 0 | 2 | |
| 5 | 1 | 0 | 0 | 0 | 1 | 0 | 2 | |
| Total | 5 | 4 | 1 | 0 | 1 | 0 | 11 | |

Not be bothered: 0, Bothered: slightly bothered [1-2-3-4-5] very bothered

TABLE 41

Being bothered with hair thickness

| At the time of entry (before start drinking) | After drinking for 4 weeks | | | | | | Total | Within-subgroup test |
|---|---|---|---|---|---|---|---|---|
| | 0 | 1 | 2 | 3 | 4 | 5 | | |
| 0 | 3 | 0 | 0 | 0 | 0 | 0 | 3 | p = 0.031 |
| 1 | 2 | 1 | 0 | 0 | 0 | 0 | 3 | |
| 2 | 1 | 1 | 0 | 0 | 0 | 0 | 2 | |
| 3 | 0 | 0 | 0 | 0 | 0 | 0 | 0 | |
| 4 | 1 | 0 | 0 | 0 | 0 | 0 | 1 | |
| 5 | 1 | 0 | 0 | 0 | 1 | 0 | 2 | |
| Total | 8 | 2 | 0 | 0 | 0 | 1 | 11 | |

Not be bothered: 0, Bothered: slightly bothered [1-2-3-4-5] very bothered

By drinking the bee product composition, there was observed a reduction in the occurrence frequency of symptoms, a suppression of the occurrence of symptoms, or an alleviation in symptoms, such as asthenopia, a cold, tinnitus, dysuria, palpitation and breathlessness, insomnia, awareness of mental stress, vertigoes, poor skin condition, loss of appetite, nausea of the chest and the stomach, constipation, numbness of hands and feet, tired feeling, decrease in motivation, or poor hair condition, and it was shown that the above various symptoms were significantly alleviated. Further, it was verified that blood pressure was significantly lowered and that total cholesterol in serum was significantly reduced by drinking the bee product composition.

The invention claimed is:
1. A composition comprising:
honey, bee pollen, royal jelly, and propolis,
wherein a content of the honey is 70% by mass or more and less than 100% by mass relative to a whole amount of the composition; a content of the bee pollen is more than 0% by mass and 10% by mass or less in terms of solid content relative to a whole amount of the composition; a content of the royal jelly is more than 0% by mass and 10% by mass or less in terms of solid content relative to a whole amount of the composition; and a content of the propolis is more than 0% by mass and 10% by mass or less in terms of solid content relative to a whole amount of the composition;
wherein the royal jelly comprises an enzyme-hydrolyzed royal jelly;
wherein the composition is for oral administration.

2. The composition according to claim 1, wherein the honey is at least one selected from the group consisting of manuka honey, acacia honey, and honeydew honey.

3. The composition according to claim 1, wherein the honey is manuka honey and acacia honey.

4. The composition according to claim 1, wherein the composition is for alleviating asthenopia, for alleviating cold symptoms, for alleviating tinnitus, for alleviating dysuria, for alleviating palpitation and breathlessness, for improving quality of sleep, for reducing mental stress, for alleviating vertigoes, for improving skin condition, for stimulating appetite, for alleviating nausea of a chest and a stomach, for improving constipation, for alleviating numbness of hands and feet, for lowering blood pressure, for reducing cholesterol, for alleviating tired feeling, for improving motivation, or for improving hair condition.

5. The composition according to claim 4, wherein the composition is food, health foods, functional foods, nutritional supplementary foods, supplements, or foods for specified health use.

6. The composition according to claim 1, wherein the content of the bee pollen is more than 2% by mass and 10% by mass or less in terms of solid content relative to a whole amount of the composition; the content of the royal jelly is more than 1% by mass and 10% by mass or less in terms of solid content relative to a whole amount of the composition; and the content of the propolis is more than 0.07% by mass and 10% by mass or less in terms of solid content relative to a whole amount of the composition.

* * * * *